United States Patent [19]

Grossman

[11] Patent Number: 4,881,553
[45] Date of Patent: Nov. 21, 1989

[54] MESH REINFORCED CONDOM

[76] Inventor: Richard A. Grossman, 1620 Forest Ave., Durango, Colo. 81301

[21] Appl. No.: 123,587

[22] Filed: Nov. 20, 1987

[51] Int. Cl.⁴ .............................................. A61F 13/00
[52] U.S. Cl. ...................................... 128/844; 604/347
[58] Field of Search ........................... 128/132 R, 844; 604/349, 351, 352, 353; 2/239, 241

[56] References Cited

U.S. PATENT DOCUMENTS

| 2,406,600 | 8/1946 | Forestiere | 128/132 R |
| 2,586,674 | 2/1952 | Lönne | 604/349 |
| 2,792,835 | 5/1957 | Ferguson | 604/212 |
| 3,521,624 | 7/1970 | Gander et al. | 604/304 |
| 3,608,552 | 9/1971 | Arthur | 604/349 |
| 3,809,090 | 5/1974 | Poulacs et al. | 604/347 |
| 3,951,141 | 4/1976 | Kopelowicz | 604/347 |
| 3,998,228 | 12/1976 | Poidomani | 604/351 |
| 4,320,752 | 3/1982 | Comparetto | 604/349 |
| 4,553,968 | 11/1985 | Komis | 604/353 |

Primary Examiner—Richard J. Johnson
Assistant Examiner—Charles H. Sam
Attorney, Agent, or Firm—Donald W. Erickson

[57] ABSTRACT

An improved condom having an elastic mesh as an integral part of the walls of the condom. The elastic mesh reinforces the latex walls of the condom making the condom less susceptible to breakage without loss of sensitivity.

18 Claims, 1 Drawing Sheet

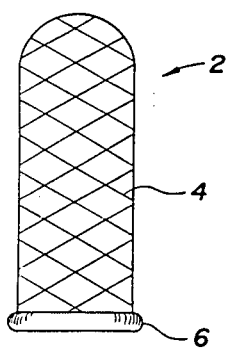
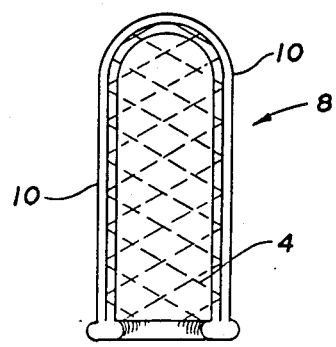
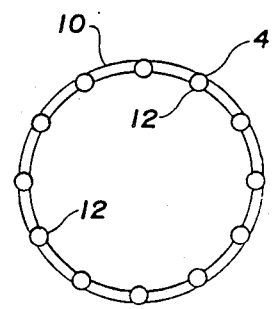
FIG. 1        FIG. 2        FIG. 3
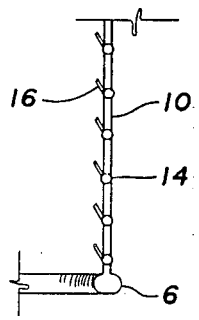
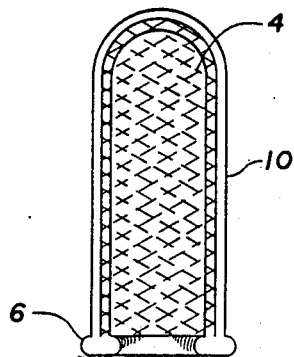
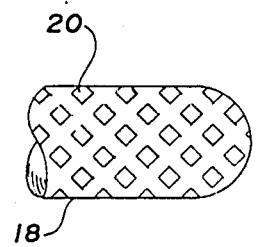
FIG. 4        FIG. 5        FIG. 6
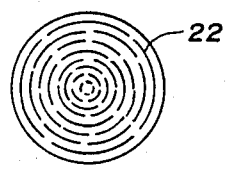
FIG. 7

MESH REINFORCED CONDOM

BACKGROUND OF THE INVENTION

Condoms in the form of a sheath, commonly made from natural rubber latex, are worn over the penis to prevent conception or venereal infection during coitus. Any failure in the integrity of the sheath walls or slippage of the sheath can defeat the purpose of the condom. Prior art approaches to making condoms safer by reducing the risk of breakage of the sheath walls are described by McEwen, U.S. Pat. No. 2,577,345 and Lonne, U.S. Pat. No. 2,586,674. McEwen describes reinforcement of a condom by use of a cushioned cap positioned over the upper or closed end portion of the condom. The cushioned cap is cumbersome to manufacture and, in addition, reduces the sensitivity of the condom. Lonne describes a condom having a series of diagonally or annularly extending hollow protrusions of less tension (greater elasticity) than the latex walls which are intended to receive discharged sperm and thereby lessen the risk of rupture of the condom. This method of increasing safety, however, makes the condom more difficult to manufacture. To reduce the risk of slippage of a condom during coitus, Conway et al., U.S. Pat. No. 4,638,790, describe a condom or a contraceptive hood which is adhesively secured to the penis. In addition to the inconvenience of the adhesive material, the aforementioned condom is rather complex to manufacture.

SUMMARY OF THE INVENTION

The present invention is directed at an improved condom characterized by substantially reduced risk of breakage and slippage. More particularly, the present invention is directed at an improved condom which comprises a phallic shaped latex sheath having a reinforcing elastic mesh embedded in the walls of the sheath, the elasticity of the mesh being about equal to or less than the elasticity of the latex sheath. The mesh may be co-extensive with the length of the sheath or may be embedded in only the upper one half or upper one third end of the sheath. The upper end is with reference to the closed end of the sheath.

BRIEF DESCRIPTION OF THE DRAWINGS

FIG. 1 is a side view of an elastic mesh for preparation of a condom in accordance with the present invention;

FIG. 2 is a vertical section view of a condom of the present invention utilizing the elastic mesh of FIG. 1;

FIG. 3 is an enlarged cross section view of a condom of the present invention.

FIG. 4 is a vertical section view of the side wall of another embodiment of a condom of the present invention;

FIG. 5 is an elevational view of a condom of the present invention wherein the elastic mesh is a finer mesh than the coarse mesh shown in FIG. 2.

FIG. 6 is a partial side view of a reinforcing mesh of the present invention; and FIG. 7 is a top view of an elastic disk for forming the mesh of FIG. 6.

DETAILED DESCRIPTION OF THE INVENTION

Referring to FIG. 1, there is shown an elastic reinforcing mesh 2 comprising threads 4 and an elastic bead or rim 6. The elastic bead serves to securely hold the mesh on the condom former or mandrel during manufacture such as while dipping the mandrel in liquid latex to form a reinforced condom 8 as shown in FIG. 2. The mesh becomes an integral part of the condom with the mesh embedded in the latex walls 10. The mesh, as shown in FIGS. 1 and 2, gives lateral and vertical reinforcement to the condom which greatly reduces the risk of tearing or rupturing of the condom walls. In this regard, the elasticity of the mesh threads 4 should be about equal to the elasticity of the latex walls. Alternatively, in fulfilling its reinforcement function, the mesh elasticity can be somewhat less than the elasticity of the latex. For example, the mesh elasticity can be on the order of about 5 to 75 percent less than the elasticity of the condom walls, more usually about 5 to 25 percent less. As a guide, the modulus of elasticity difference between the mesh and latex walls should not be too substantial in order to minimize the risk of voids and tearing at the juncture of the mesh threads and latex. The mesh can be coarse as shown in FIG. 1, fine as shown in FIG. 5, or mesh sizes intermediate to coarse and fine. The mesh can be made from an elastic thread such as natural rubber thread or other elastic material such as a synthetic rubber, silicone elastomer, or a blend of a fiber such as cotton and a polymer such as rubber. The bead or rim 6 can be made of the same or different material as the mesh thread. Alternatively, a reinforcing mesh without a bead 6 can be placed on the mandrel and the bead formed while dipping of the mandrel in latex to form the condom. The thickness of the thread forming the mesh can be the same as the thickness of the latex wall or slightly less or greater thickness. As shown in FIG. 2, the mesh thickness is slightly less than the latex wall. This form provides a smooth surface on the inner and outer walls of the condom. By using a mesh thread 4 that is slightly thicker than the latex wall, a texture on the inner wall surface as at 12, FIG. 3, can be made. This textured embodiment is advantageous in that it not only reinforces the condom but substantially reduces the risk of slippage of the condom from the penis during coitus. To further enhance nonslippage of the condom, the embodiment of FIG. 4 is provided within small, slanted projections 16 on the inner wall are formed. The small projections are slanted toward the upper or closed end of the condom and inhibit the condom from sliding off the penis. The projections can be formed as part of the mesh thread 14. In production, the condom may be made with the projections on the outside and then it is turned inside out during or after removal from the mandrel.

Latex condoms have thin walls on the order of 0.02–0.09 mm. depending on the manufacturer. A thin wall is desirable because of its effect on sensitivity or transmission of sensation. The present invention permits the use of very thin walls in view of the strength provided by the elastic reinforcing mesh. Thus, the condoms of the present invention have substantially improved sensitivity.

In another embodiment of the present invention, FIG. 6, the reinforcing mesh is made from a flat sheet of thin plastic film such as a natural rubber latex disk shown in FIG. 7. The elastic disk has slits 22 punched out prior to stretching the disk over the mandrel which results in formation of the holes 20 when the disk is stretched over the mandrel. This embodiment also permits the use of very thin condom walls to enhance the transmission of sensation without sacrifice of safety.

The elasticity of the film 18 should be equal to or somewhat less than the elasticity of the latex forming the condom walls. The size of the holes can vary. Generally, the holes 20 will be within the dimensions of about 2.0 to 15.0 mm.

Referring to FIG. 4, as shown, the projections 16 can be formed as part of the mesh thread 14. In another embodiment, the projections 16 are formed as a part of the latex wall 10, with or without the presence of a reinforcing mesh. In another embodiment, when the reinforcing mesh is made from a flat sheet of thin plastic film, the projections 16 can be either embossed on the plastic film or formed by flaps of the film between slits 22. The slanted projections can be generally uniformly distributed over the sheath wall. Spacing of the projections does not appear to be critical. A spacing of about 2 to 10 mm. between projections can be used. The length of the projections can range from about 2 to 8 mm., more usually, about 3 to 6 mm. The projections can be distributed over the entire surface of the sheath walls or only part of the surface such as the upper one-half or one-third.

The term "mesh", as used herein and in the appended claims, refers to a material of open texture with generally evenly spaced holes formed from a woven, knit or knotted material or a material in which holes have been cut or punched.

What is claimed is:

1. An elastic mesh, in the size and shape of a condom, which is useful for the production of a latex condom wherein all walls of the condom are reinforced, said mesh having an elasticity about equal to the elasticity of latex of a condom and said mesh being open at its lower end and closed at its upper end.

2. The elastic mesh according to claim 1 wherein the open end thereof is provided with an elastic bead.

3. The elastic mesh according to claim 1 wherein the holes of the mesh have a size within the range of about 2.0 mm. to 15.0 mm.

4. The elastic mesh according to claim 3 wherein the size of the holes is from about 4.0 mm. to 10.0 mm.

5. The elastic mesh according to claim 1 wherein the threads of the mesh have small projections which slant toward the closed end of the mesh.

6. The elastic mesh according to claim 1 wherien the mesh is made of natural rubber latex thread.

7. An improved condom, said condom having a tubular latex wall, and being open at its lower end and closed at its upper end, wherein the tubular wall of the condom is reinforced by
an elastic mesh embedded in said wall, the elasticity of the mesh being about equal to or less than the elasticity of said wall.

8. The improved condom according to claim 7 wherein the elastic mesh has a thickness greater than the thickness of the condom wall.

9. The improved condom according to claim 7 wherein the thickness of the elastic mesh is less than the thickness of the condom wall.

10. The improved condom according to claim 7 wherein the condom wall, on the inner wall, is provided with small, slanted projections, said projections being slanted toward the closed end of the condom.

11. The improved condom according to claim 7 wherein the elastic mesh is embedded in only the upper half of the condom wall.

12. The improved condom according to claim 7 wherein the elasticity of the mesh is from about 5 to 75 percent less than the elasticity of the condom wall.

13. The improved condom according to claim 7 wherein the elasticity of the mesh is from about 5 to 25 percent less than the elasticity of the condom wall.

14. The improved condom according to claim 7 wherein the elastic mesh has a mesh size of about 2 to 15 mm.

15. The improved condom according to claim 7 wherein the elastic mesh has a mesh size of about 4 to 10 mm.

16. The improved condom according to claim 10 wherein the slanted projections are an integral part of the elastic mesh.

17. The improved condom according to claim 10 wherein the slanted projections are provided only in the upper half of the condom wall.

18. The improved condom according to claim 7 wherein the elastic mesh and condom walls are made of natural rubber latex.

* * * * *